United States Patent [19]
Voigt et al.

[11] Patent Number: 5,055,301
[45] Date of Patent: Oct. 8, 1991

[54] USE OF DEXTRAN SULPHATE FOR THE TREATMENT OF HUMAN PROSTATIC CARCINOMA

[75] Inventors: Klaus-Dieter Voigt; Cornelius Knabbe, both of Hamburg, Fed. Rep. of Germany

[73] Assignee: Entec Gesellschaft fur Endokrinologische Technologie m.b.h., Hamburg, Fed. Rep. of Germany

[21] Appl. No.: 466,617

[22] Filed: Jan. 17, 1990

[30] Foreign Application Priority Data

Jan. 20, 1989 [DE] Fed. Rep. of Germany ....... 3902021
Sep. 20, 1989 [DE] Fed. Rep. of Germany ....... 3935855

[51] Int. Cl.$^5$ ..................... A61F 13/00; A61K 31/715
[52] U.S. Cl. .................................... 424/422; 424/435; 424/436; 514/59; 536/51
[58] Field of Search .................. 514/59; 424/422, 436, 424/435; 536/51

[56] References Cited

U.S. PATENT DOCUMENTS 4,462,987  7/1984  Bonifacio ............................. 424/99
4,780,313  4/1988  Koichiro et al. ..................... 424/88

FOREIGN PATENT DOCUMENTS 1951822  4/1971  Fed. Rep. of Germany .

OTHER PUBLICATIONS

Parish et al. Chem. Absts. #108187, 110, 1989.
Niitani et al., Chem. Absts. #106538q, 82, 1975.
Zimmermann et al., Chem. Absts. 191381f 98, 1983.
Roth All About Cancer, Stickley Co. PA, 1985 p. 272.

Primary Examiner—Thurman K. Page
Assistant Examiner—G. S. Kishore
Attorney, Agent, or Firm—Nixon & Vanderhye

[57] ABSTRACT

The invention relates to the use of dextran sulphate, optionally in combination with anti-androgen agents, for the treatment of the human prostatic carcinoma. Inhibition of the growth of both androgen-dependent and androgen-independent carcinoma cells is achieved according to the invention. The invention therefore leads to a significant improvement in the possible therapies for human prostatic carcinoma.

10 Claims, 1 Drawing Sheet

USE OF DEXTRAN SULPHATE FOR THE TREATMENT OF HUMAN PROSTATIC CARCINOMA

BACKGROUND OF THE INVENTION

Prostatic carcinoma (PCA) is of considerable importance in the cancer statistics of Western countries. In the Federal Republic of Germany alone there are about 8000 fatalities each year. The incidence, approx. 10 % of all malignant diseases in men, makes PCA the second most frequent tumour in the male sex. For example, 96000 new cases and 26000 fatalities were recorded in the USA in 1987.

In spite of intensive efforts in research and clinical treatment, the age-adjusted mortality rate in the USA, for example, remained largely constant from 1950 to 1980, while in smaller European countries a marked increase has even been observed, which because of its higher incidence in older age groups must be seen in relation to a shift in the age structure of the population.

The androgen-dependence of prostatic carcinoma has been known in scientific literature since the investigations of Huggins and Hodges (cf. Cancer Res. 1, 293–297 (1941)).

Further to these studies, an endocrine treatment of the prostatic carcinoma was proposed in which it was shown that a regression of the tumour can be achieved by androgen-ablation (cf. Emmett et al., J.Urol. 83, 471–484 (1960)). In addition to the local displacement of the androgen from its cellular receptor by anti-androgens, such as flutamide or cyproterone acetate, the direct suppression of circulating androgens by surgical means, such as orchietomy, hypophysectomy or adrenalectomy, or by the administration of substances such as diethylstilbestrol or aminoglutethimide, has therefore become usual in the treatment of advanced prostatic carcinomas.

This endocrine treatment results in subjective success in 60 to 80% of cases. However, an objective improvement occurs in only 20 to 40% of patients. In addition, a considerable lengthening of the symptom-free interval may be achieved.

The androgen-ablative therapy does not, however, result in the patients being cured. The majority of patients die after an initial period of remission, usually following the almost obligatory conversion of the tumour from the initially hormone-dependent state into the hormone-independent state.

The aetiology of this conversion of the tumour into the androgen-independent state has not yet been finally clarified, although more recent investigations indicate an initial heterogeneity of the tumour. That is to say, both androgen-dependent and androgen-independent cells can be detected in the tumour. Even the recently disclosed therapy with gonadotropin-releasing hormone analogues (GnRH-analogues), such as leuprolide (cf. Schally et al., Int.J.Gynaecol.Obstet. 18, 318–324, (1980)) is based on a reduction of the peripheral androgen level by inhibition of the pituitary-gonad axis. The main advantage of this form of therapy compared with conventional treatment lies in its reduced side-effects, while it is not possible to prove objective superiority, for example, over therapy with diethylstilbestrol (cf. inter alia Tolis, G. et al., Proc. Nat. Acad. Scien. 79, 1658–1662 (1982)).

Finally, the "complete" androgen-ablation through the combination of GnRH-analogues with non-steroidal anti-androgens, as proposed by Labrie, has not as yet resulted in any clear improvement in the laboratory or in clinical studies (cf. Labrie et al., J.Steroid.Biochem. 23, 833–841 (1985)).

In summary, it can therefore be said that none of the newer therapy regimens have lead to a significant improvement in the remission and survival rate compared with classical endocrinological therapy.

DETAILED DESCRIPTION OF THE INVENTION

Figure 1:
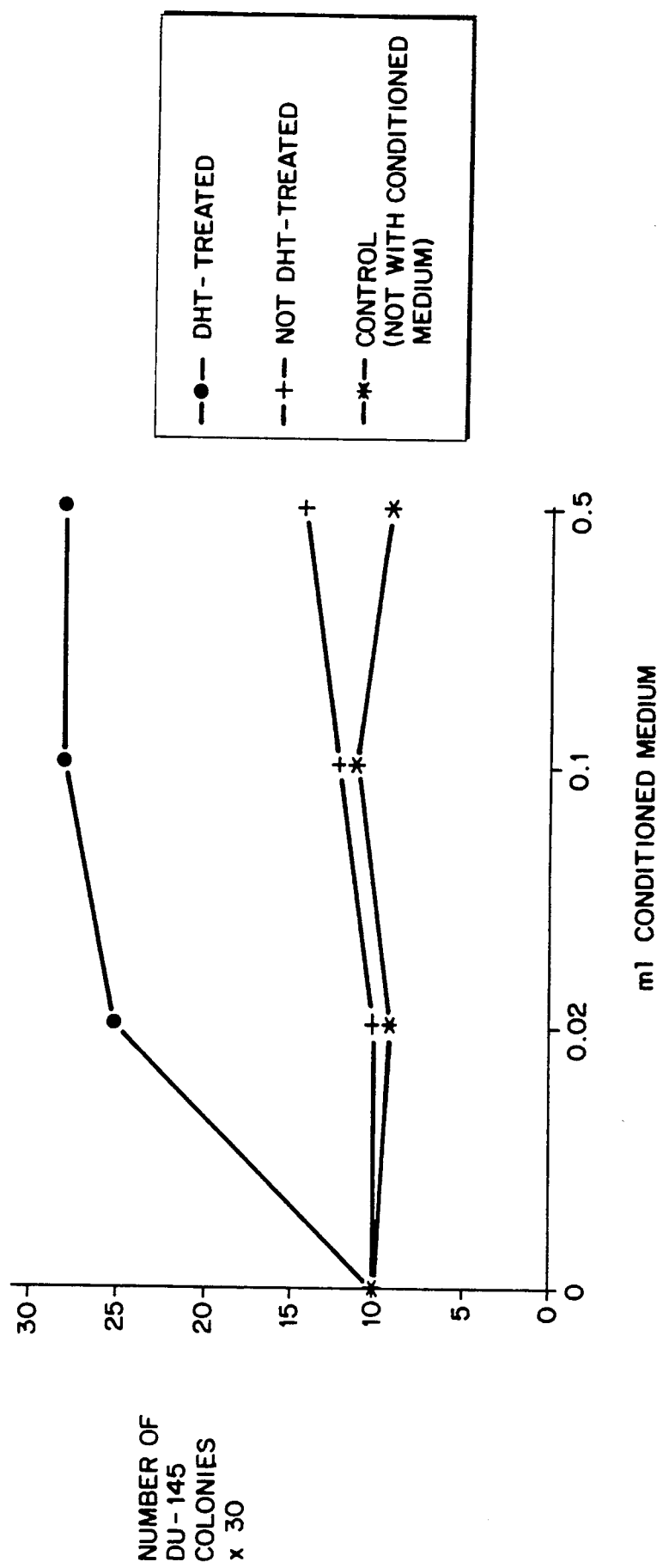
FIG. 1 is a graph showing androgen induction of growth-factor activity in a conditioned medium of LNCaP cells reporting the results of Example 2.

It is therefore an object of the invention to provide agents for the treatment of human prostatic carcinoma which simultaneously treat the androgen-dependent and the androgen-independent cells and therefore lead to an improvement in the objective remission rate and the survival period of the patient affected.

To solve this problem it is according to the invention proposed to use dextran sulphates, optionally in combination with anti-androgen agents, for the treatment of human prostatic carcinoma.

Surprisingly, it has been found according to the invention that dextran sulphates are capable of inhibiting the proliferation of both androgen-dependent and androgen-independent human prostatic carcinoma cells.

Dextran sulphates are sulphuric acid esters of dextran; methods to prepare the same are well known to the person skilled in the art. Preferably the dextran sulphates used in the invention are in the form of sodium salts and they have an average molecular weight of 5000 to 500 000. In a particularly preferred embodiment of the invention dextran sulphates having an average molecular weight of about 5000 to 60 000 are used. Surprisingly these substances can inhibit both androgen-dependent human prostatic carcinoma cell lines (LNCaP-cells) and androgen-independent prostatic carcinoma cell lines (DU-145) (cf. Table 2). The results presented in Table 2 were obtained using a dextran sulphate having an average molecular weight of about 5000. Similar results were obtained with dextran sulphates of different molecular weights (e.g. 8000 and 500 000).

In this context it was possible to show for the first time according to the invention that the androgen growth control of the human prostatic carcinoma is effected by the regulation of autocrinal growth factors (FIG. 1). Further it was possible to show for the first time that, when androgen-dependent cells are present, this regulation surprisingly also affects androgen-independent cells (cf. Table 1), and that the growth of both cell types can be inhibited by dextran sulphate (cf. Table 2).

Surprisingly, it has, however, also emerged that the androgen-dependent carcinoma cells have an additional regulation system, which is independent of growth factors (cf. Table 3) and which cannot be influenced with dextran sulphate. While in fact the growth of these cells in vitro in the absence of androgens is almost completely inhibited, even high doses of dextran sulphate cannot inhibit their proliferation to this extent when in the presence of androgens (5-alpha-dihydro-testosterone).

The consequence of this for the therapy proposed according to the invention is that, when androgen-dependent and androgen-independent cells are present at the same time, pharmaceutical formulations are used which contain a combination of dextran sulphate and anti-androgenic agents. Useful anti-androgenic agents are such agents, which can be combined with dextran sulphate, preferably within fixed combinations. Preferred agents are e.g. anti-androgenics as cyproterone acetate or flutamide inhibitors of the hypophyseal gonadotropine secretion, e.g. LH-RH-agonists or -antagonists as well as inhibitors of the steroid metabolizing enzymes, e.g. of 5-alpha-reductase or aromatase, 5-alpha-reductase inhibitors being particularly preferred. It is also possible to use more than one anti-androgenic agent in one formulation or package together with the dextran sulphate.

The aforementioned anti-androgenic agents can be present together with the dextran sulphate either in a fixed combination or formulated seperately within a package. The dosage amounts of the anti-androgenic agents can e.g. correspond to the amounts used when the same are applied alone, such amounts being well known to the skilled person; in some cases it will be possible to lower the usual dosage amounts of anti-androgenics.

On the other hand, preparations which contain only dextran sulphates as the active agent can be used for the treatment of the hormone-independent form of the prostatic carcinoma, dosage amounts of about 2 to 40 mg/kg/day of dextran sulphate being preferred both in combination preparations as well as in formulations containing dextran sulphate alone. For manufacturing the pharmaceutical preparations of the invention known pharmaceutically acceptable carrier substances and additives are used and are formulated according to known methods to obtain a suitable preparation for the respective desired pharmaceutical presentation, which can be for local, oral, parenteral, intraperitoneal or rectal application. According to a particularly preferred embodiment of the invention the active agent(s) is(are) applied parenterally.

The invention is further illustrated in the following by means of examples.

In the following examples the androgen-dependent human PCA cell line LNCaP (cf. Horoszewicz et al., Cancer Research 43, 1809–1818 (1983)), and the androgen-independent human prostatic carcinoma cell line DU-145 ATCC No. HTB81 were used, and cultivated in a DMEM culture medium enriched with 10 % of foetal calf serum as a continuous culture.

For each of the growth tests, the culture medium was largely freed from endogenic steroids (cf. Darbre et al., Cancer Res. 43, 349–354 (1983).

EXAMPLE 1

This example investigated the effect on DU-145 cells of 5-alpha-dihydro-testosterone, both alone and in the presence of LNCaP cells.

The experiment was carried out in a 4-chambered Petri dish, previously wetted with 0.1 mg/ml poly-D-lysin.

1000 DU-145 cells were inoculated into each of two chambers. The cells in one of the chambers were treated with DHT (5-alpha-dihydro-testosterone) in an end-concentration of $10^{-8}$ in ethanolic solution; while the cells in the second chamber were treated only with the solvent for control purposes. The end-concentration of the ethanol was 0.1% in both batches.

The number of DU-145 colonies with more than 50 cells after 5 days was selected as the growth indicator, and was microscopically determined after fixing with methanol and staining with amido-black.

In a further batch, two chambers of the Petri dish were each inoculated with $5 \times 10^5$ LNCaP cells, and the cells in one of the chambers were stimulated with DHT in ethanolic solution as described above, while the second chamber again served as a control.

The two remaining chambers were inoculated with DU-145 cells as above, but without further additives.

After 24 hours the dividing wall between a chamber inoculated DU-145 cells and a chamber inoculated with LNCaP cells was perforated so that a DU-145 chamber could be in contact via the medium with a LNCaP chamber. The growth rates in each of the chambers were determined again.

The results from the two batches are reproduced in Table 1.

TABLE 1

| Growth of DU-145 in co-culture with LNCaP | | |
|---|---|---|
| | Treatment with ethanol (= control) | Treatment with DHT |
| no LNCaP in co-culture (= control) | 107 | 104 |
| LNCaP in co-culture | 136 | 213 |

The results indicate the DHT alone, as expected, does not affect the DU-145 cells, while a slight increase in growth can be observed in the presence of LNCaP cells without androgenic stimulation, which rises considerably with androgenic stimulation.

One can conclude from these results that the activity formed by the LNCaP cells under the influence of DHT also stimulates the growth of androgen-independent cells.

EXAMPLE 2

In a further experiment, serum-free, conditioned medium was obtained from LNCaP cells with and without androgenic stimulation according to a process modified according to Dickson et al., Endocrinology 118, 138–142 (1986).

The conditioned medium was tested to examine its growth-factor activity in a soft-agar assay with DU-145 cells, according to the process explained in Example 3 below.

The results are reproduced in FIG. 1. They confirm the induction by androgens of growth-factor activities in a medium of LNCaP cells.

The peptide nature of the growth-factor activities was proved by protease and heat activation.

EXAMPLE 3

The growth-inhibiting effect of dextran sulphate (molecular weight 5000) on both cell types was proved in the soft-agar assay (modified according to Hamburger and Salmon, Science 197, 461 (1977)).

0.8 ml of an upper layer consisting of DMEM, 0.4 % bacto-agar, 10 % foetal calf serum, and the sample to be tested ($10^{-8}$M DHT or ethanol and/or dextran suphates) and the indicator cells (15,000 DU-145 or LNCaP cells) was placed in 35 mm dishes on an already hardened lower layer of 1.0 ml DMEM with 0.6 % agar and 10% foetal calf serum. The dishes were incubated for 14 days at 37° C. and 5 % carbon dioxide tension. Cell colonies larger The results are reproduced in Tables 2 and 3.

TABLE 2

| | Growth of LNCaP and DU-145 cells | | |
|---|---|---|---|
| | — | Dextran sulphate 10 μg/ml | Dextran sulphate 100 μg/ml | Dextran sulphate 1000 μg/ml |
| DU-145 | 380 | 350 | 125 | 60 |
| LNCaP | 480 | 360 | 50 | 50 |

TABLE 3

| | Growth of LNCaP cells | | |
|---|---|---|---|
| | — | Dextran sulphate 10 g/ml | Dextran sulphate 100 μg/ml | Dextran sulphate 1000 μg/ml |
| Ethanol | 480 | 360 | 50 | 50 |
| $+10^{-8}$ M DHT | 900 | 560 | 240 | 200 |

As Table 2 shows, the growth of both LNCaP cells and DU-145 cells is clearly inhibited by dextran sulphate at a concentration of 100 μg/ml.

In contrast, it can be seen from Table 3 that even dextran sulphate concentrations of 1000 μg/ml inhibit the proliferation of LNCaP cells only partially in the presence of DHT. One can conclude from this that the cells have a dextran-sulphate-resistant regulation system, the biological value and biochemical identity of which are as yet unclarified.

The maximum inhibition of LNCaP cells is accordingly only possible by adding dextran sulphate in the absence of DHT (androgen removal).

Similar results were obtained with dextran sulphate molecular weight 500 000.

We claim:

1. A method of treating human prostatic carcinoma comprising administering to a patient having a human prostatic carcinoma susceptible to treatment a pharmaceutical composition consisting essentially of dextran sulfate in an amount effective to inhibit the proliferation of human prostatic carcinoma cells.

2. The method of claim 1, in which the carcinoma is androgen-independent human prostatic carcinoma.

3. The method of claim 1, in which the average molecular weight of the dextran sulphate is about 5,000 to about 500,000.

4. The method of claim 2, in which the average molecular weight of the dextran sulphate is about 5,000 to about 500,000.

5. The method of claim 1, in which the patient is administered about 2 to about 40 mg/kg/day dextran sulphate based upon the patient's body weight in kg.

6. A method of treating human prostatic carcinoma in a patient having both androgen-dependent and androgen-independent human prostatic carcinoma comprising administering to the patient a pharmaceutical composition consisting essentially of, in combination amounts of both an anti-androgenic agent and dextran sulphate effective to inhibit the proliferation of both androgen-dependent and androgen-independent human prostatic carcinoma cells.

7. The method of claim 6, in which the dextran sulphate and anti-androgenic agent are administered concurrently in the same pharmaceutical composition.

8. The method of claim 6, in which the average molecular weight of the dextran sulphate is about 5,000 to 500,000.

9. The method of claim 8, in which the average molecular weight of the dextran sulphate is about 5,000 to 60,000.

10. The method of claim 6, in which the patient is administered about 2 to about 40 mg/kg/day dextran sulphate based upon the patient's body weight in kg.

* * * * *